(12) United States Patent
Wang et al.

(10) Patent No.: US 9,720,008 B2
(45) Date of Patent: Aug. 1, 2017

(54) AUTOMATIC ANALYZERS AND REAGENT WHEELS THEREOF

(71) Applicant: SHENZHEN MINDRAY BIO-MEDICAL ELECTRONICS CO., LTD., Shenzhen (CN)

(72) Inventors: Zhihong Wang, Shenzhen (CN); Shicai Li, Shenzhen (CN); Xingcai Zhu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 25 days.

(21) Appl. No.: 14/516,403

(22) Filed: Oct. 16, 2014

(65) Prior Publication Data

US 2015/0037211 A1 Feb. 5, 2015

Related U.S. Application Data

(63) Continuation of application No. PCT/CN2013/074283, filed on Apr. 17, 2013.

(30) Foreign Application Priority Data

Apr. 17, 2012 (CN) .......................... 2012 1 0112935

(51) Int. Cl.
*G01N 35/04* (2006.01)
*G01N 35/02* (2006.01)
*B01L 9/06* (2006.01)

(52) U.S. Cl.
CPC .............. *G01N 35/025* (2013.01); *B01L 9/06* (2013.01); *G01N 35/04* (2013.01);
(Continued)

(58) Field of Classification Search
CPC ... G01N 2035/0439; G01N 2035/0443; G01N 2035/0444; G01N 2035/0453; G01N 2035/0455
(Continued)

(56) References Cited

U.S. PATENT DOCUMENTS 4,906,433 A * 3/1990 Minekane ............ G01N 35/025
   422/561
5,051,238 A * 9/1991 Umetsu ................ G01N 35/025
   422/64
(Continued)

FOREIGN PATENT DOCUMENTS

CN 1963527 A 5/2007
CN 101169450 A 4/2008
(Continued)

*Primary Examiner* — Jill Warden
*Assistant Examiner* — Dwayne K Handy
(74) *Attorney, Agent, or Firm* — Kory D. Christensen; Polsinelli LLP

(57) ABSTRACT

This disclosure provides automatic analyzers and reagent wheels thereof. The reagent wheel can have one or more rings of reagent bottle seats that may be used for placing a reagent container and distributed along a circumferential direction. An included angle may be formed between a symmetrical centerline of the reagent container placed on the reagent bottle seat and a radius of a circle where the reagent wheel is located, where the included angle is not equal to zero. Compared with the situation in which the symmetrical centerline of the reagent container overlaps with the radius of the circle where the reagent wheel is located, an improved balance can be achieved between the capacity and the diametric size of the reagent wheel, thus making an improvement in meeting application requirements of the analyzers.

5 Claims, 2 Drawing Sheets

(52) U.S. Cl.
CPC ............. *B01L 2300/0803* (2013.01); *G01N 2035/0443* (2013.01); *G01N 2035/0455* (2013.01)

(58) Field of Classification Search
USPC .................................... 422/63, 64, 560, 561
See application file for complete search history.

(56) References Cited

U.S. PATENT DOCUMENTS 5,133,936 A * 7/1992 Umetsu et al. ................ 422/64
5,985,218 A * 11/1999 Goodale ...................... 422/554

FOREIGN PATENT DOCUMENTS

| | | |
|---|---|---|
| CN | 101218027 A | 7/2008 |
| CN | 101218027 A | 7/2008 |
| CN | 201434871 Y | 3/2010 |
| CN | 101726616 A | 6/2010 |
| CN | 102221626 A | 10/2011 |
| CN | 102326087 | 1/2012 |
| CN | 102326087 A | 1/2012 |
| JP | 8-271517 A | 10/1996 |
| JP | 2010-145284 A | 7/2010 |
| WO | WO2011012657 A1 | 2/2011 |
| WO | WO2011059444 A1 | 5/2011 |

\* cited by examiner

AUTOMATIC ANALYZERS AND REAGENT WHEELS THEREOF

TECHNICAL FIELD

This disclosure generally relates to reagent wheels of automatic analyzers, and more particularly to automatic biochemical analyzers and reagent wheels thereof.

BACKGROUND

Automatic analyzer is a medical testing equipment commonly found in hospitals. Recently, since people have more demand for their own health condition, health examination involving various test items has been growing increasingly. This may therefore raise more demand on the automatic analyzer. For example, in a high-speed automatic biochemical analyzer, a reagent wheel may be highly demanded on its capacity, since more capacity can facilitate and support more test items, and can reduce a frequency of changing the reagent so as to enhance corresponding operation efficiency. The capacity of the reagent wheel may include an amount of a reagent seat arranged thereon and a volume of a reagent container that can be accommodated within each reagent seat. Generally, the larger the capacity of the reagent wheel is, the larger the size of the reagent wheel becomes. Moreover, the reagent wheel with large size may bring about a bigger operation table for the biochemical analyzer. Since operation staff (e.g., a doctor) may sometimes need to perform some operations (such as picking up or placing down the reagent) on the operation table, such table with too large size may result in inconvenient operation. For instance, it may be impossible to reach some reagent seats located in the rear side (the high-speed biochemical analyzer can only be operated from its front side at most of the time, since its rear side is located against the wall and its bilateral sides may be coupled to other module(s)). In addition, the whole equipment may become larger when the operation table is larger in size, which not only causes inconvenience in transportation and placement but also reduces consumer acceptability. Therefore, it is needed to improve the capacity of the reagent wheel while achieving small operation table simultaneously.

SUMMARY OF THIS DISCLOSURE

This disclosure provides reagent wheels of automatic analyzers that may have both improved capacity and controllable diametric size, thereby meeting the requirements on the capacity and the operability of the analyzers.

In one aspect, this disclosure can provide a reagent wheel of an automatic analyzer. One or more rings of reagent bottle seats for placing a reagent container can be distributed on the reagent wheel along a circumferential direction. The reagent container placed on the reagent bottle seats can have a distal end face away from a circle center of the reagent wheel and a proximal end face proximate to the circle center of the reagent wheel, where a line segment representing a vertical distance between the distal end face and the proximal end face can be defined as a distance line. There can be an included angle ranging from about 0 degree to about 180 degree between the distance line of the reagent container placed on at least one ring of reagent bottle seats and a radius of the circle where the reagent wheel is located. Such arrangement (i.e., the included angle) between the distance line and the radius of the reagent wheel may be equivalent to rotate the reagent container in the plane of the reagent wheel by the included angle along a clockwise or an anticlockwise direction, so that the respective reagent container can be arranged obliquely.

In some embodiments, approximately equal included angles can be formed between the distance lines of the respective reagent containers placed on a same ring of reagent bottle seats and the radius of the circle where the reagent wheel is located.

In some embodiments, the reagent container may be bilaterally symmetrical with respect to a symmetrical centerline, where the distance line can be the symmetrical centerline.

In another aspect, a reagent wheel of an automatic analyzer can include a circle center and one or more rings of reagent bottle seats used for placing a reagent container, where the reagent bottle seats may be distributed around the circle center of the reagent wheel along a circumferential direction. The reagent container placed on the reagent bottle seats can have a reagent container centerline, and each reagent container centerline may correspond to a radius of the reagent wheel. For the reagent container placed on at least one ring of reagent bottle seats, its reagent container centerline may be arranged obliquely towards one side of its corresponding radius, and an included angle ranging from about 0 degree to about 180 degree can be formed between the reagent container centerline and the corresponding radius.

In some embodiments, the reagent container centerline may be equivalent to the above-described distance line. The reagent container centerline can determine a longitudinal direction of the reagent container, and can divide the reagent container into symmetrical or asymmetrical left and right halves.

In some embodiments, non-zero included angle can be formed between the reagent container centerline and the radius of the reagent wheel. In this situation, it may be equivalent to rotate the reagent container on the reagent bottle seat by the non-zero included angle along a clockwise or an anticlockwise direction, so that each reagent contained can become oblique.

In some embodiments, each reagent container centerline may be arranged obliquely towards the same side of its corresponding radius, i.e., a whole ring of reagent containers may become clockwise or anticlockwise oblique.

For the respective reagent container that may be located by an included angle with respect to the radius of the reagent wheel, its proximal end face proximate to the circle center of the reagent wheel can be located on a circumference, while its distal end face away from the circle center of the reagent wheel may be located on another circumference. That is, the reagent container placed on a same ring of reagent bottle seats can be located between such two circumferences.

The reagent bottle seat can have symmetrical or asymmetrical structure.

The reagent container can have symmetrical structure. That is, the reagent container can be symmetrical with respect to the symmetrical centerline that can be the reagent container centerline. Alternatively, the reagent container can have asymmetrical structure. The reagent container centerline can completely or substantially overlap with a centerline of the reagent bottle seat.

In still another aspect, a reagent wheel of an automatic analyzer can include two rings (i.e., an inner ring and an outer ring) of reagent bottle seats. Each of the reagent bottle seats may be used for placing a reagent container. Here, a symmetrical centerline of the respective reagent container placed on the inner ring can overlap with a radius of the reagent wheel, while a symmetrical centerline of the respective reagent container placed on the outer ring may have a certain included angle with respect to the radius of the reagent wheel. Further, the included angle between the symmetrical centerline of the respective reagent container on the outer ring and the radius of the reagent wheel can be the same as each other.

In some embodiments, same reagent containers can be placed on the two rings. As required, the two rings of reagent bottle seats can be designed to support the reagent container with different shapes and/or volumes.

In various embodiments of this disclosure, the automatic analyzer may be equipped with two of the above-described reagent wheels, and based on an overall layout, the two reagent wheels can be arranged one behind the other on a table with respect to an operator. Double-ring reagent wheel can already meet the demand on the capacity of the reagent wheel in high-speed analyzers, and may even have some capacity margin. Therefore, when utilizing such reagent wheel in which the angle can be formed between the symmetrical centerline of the reagent container on the outer ring and the radius of the reagent wheel, the outer-ring capacity of the reagent wheel can be decreased to a certain extent and the diametric size of the reagent wheel can also be reduced effectively, thereby meeting users' demand on the capacity of the reagent wheel and facilitating the uses' operations including picking up or placing down the reagent.

In order to realize larger test speed, two sets of test systems may usually be integrated into a single high-end automatic analyzer. In this case, one common method is to have the reagent on inner and outer rings of the reagent wheel to respectively correspond to the two sets of test systems in the same analyzers. Accordingly, it may be required that a total capacity of both the inner and the outer rings of the reagent wheel should be designed to be large enough, and the capacity of the inner and the outer rings should be as close as possible. That is, the reagent wheels corresponding to the two sets of test systems should have little difference in their capacities, so that they can support equivalent number of test items. In this way, an optimal test efficiency can be realized when the two sets of test systems work simultaneously. This disclosure may be suitable for the following situation: the outer ring may have more reagent seats (i.e., the reagent bottle seat) when compared with the inner ring due to larger diametric size of the outer ring. Herein, the symmetrical centerline of the reagent container on the outer ring can be set to have a certain included angle with respect to the radius of the reagent wheel. Accordingly, based on that the inner ring may support the same reagent containers, the outer-ring capacity of the reagent wheel can be properly decreased, the capacity difference between the inner ring and the outer ring of the reagent wheel can be reduced, and the diametric size of the reagent wheel can be reduced simultaneously. If the reagent wheels are arranged one behind the other, the reagent wheel with smaller size can particularly improve the operability of the analyzer.

DETAILED DESCRIPTION

This disclosure can be further described below in detail with reference to figures and specific embodiments.

This disclosure can be suitable for various automatic analyzers, and more particularly for high-end automatic analyzers. Generally, at least two reagent wheels and at least one reaction wheel are disposed within the high-end automatic analyzer, where the two reagent wheels may be commonly arranged on the same side of the reaction wheel, and the two reagent wheels may be arranged one behind the other. Under this arrangement, reagent replacement operability for the reagent wheel located in the rear side is directly affected by a size of the reagent wheel located in the front side. In particular, when multiple modules are interconnected therewith, the automatic analyzer cannot be operated from its lateral sides, and the reagent can only be picked up or placed down from the front side of the rear side of the analyzer. Balance should thus be considered for the operability of the reagent wheel in the rear orientation and the total capacity of the reagent wheel. Various embodiments of this disclosure can provide a biochemical analyzer considering both the capacity and the operability of the reagent wheel.

Figure 1:
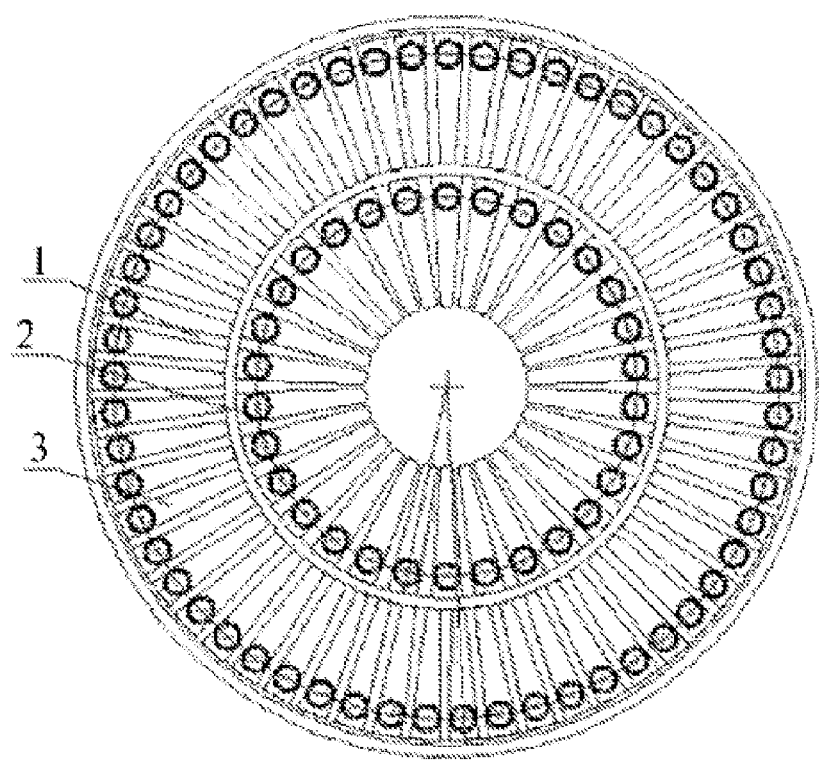
FIG. 1 is a top-down structure diagram for an existing reagent wheel.

In addition, these two reagent wheels arranged one behind the other may be integrated into the same high-speed biochemical analyzer so as to support two sets of test systems. Double rings (i.e., an inner ring and an outer ring) of reagent seats, for example, can be arranged on both of the reagent wheels for achieving larger capacity of the reagent wheel, where the inner and the outer rings can respectively correspond to the two sets of test systems. For the purpose that the two test systems can support equivalent number of test items, it may be required that a total capacity of the reagent wheel should be large enough and the capacity difference between the inner ring and the outer ring should be as small as possible. In this way, an optimal test efficiency can be realized when the two sets of test systems work simultaneously. FIG. 1 is a top-down structure diagram for an existing reagent wheel. The reagent wheel can include an inner ring and an outer ring, where an outer-ring reagent bottle seat 1 can be distributed on the outer ring, and an inner-ring reagent bottle seat 2 can be distributed on the inner ring. Generally, reagent bottles 3 with the same shape can be used on both the inner and the outer rings of the reagent wheel, and the reagent bottles 3 can be equally distributed thereon to form an annular arrangement. Symmetrical centerlines of the outer-ring reagent bottle seat 1 and the inner-ring reagent bottle seat 2 can overlap with a radius of the reagent wheel. With the increase in the total number of the reagent bottle seat on the inner and the outer rings, the difference between the numbers of the reagent bottle seat on the inner and the outer rings may increase as well.

Figure 2:
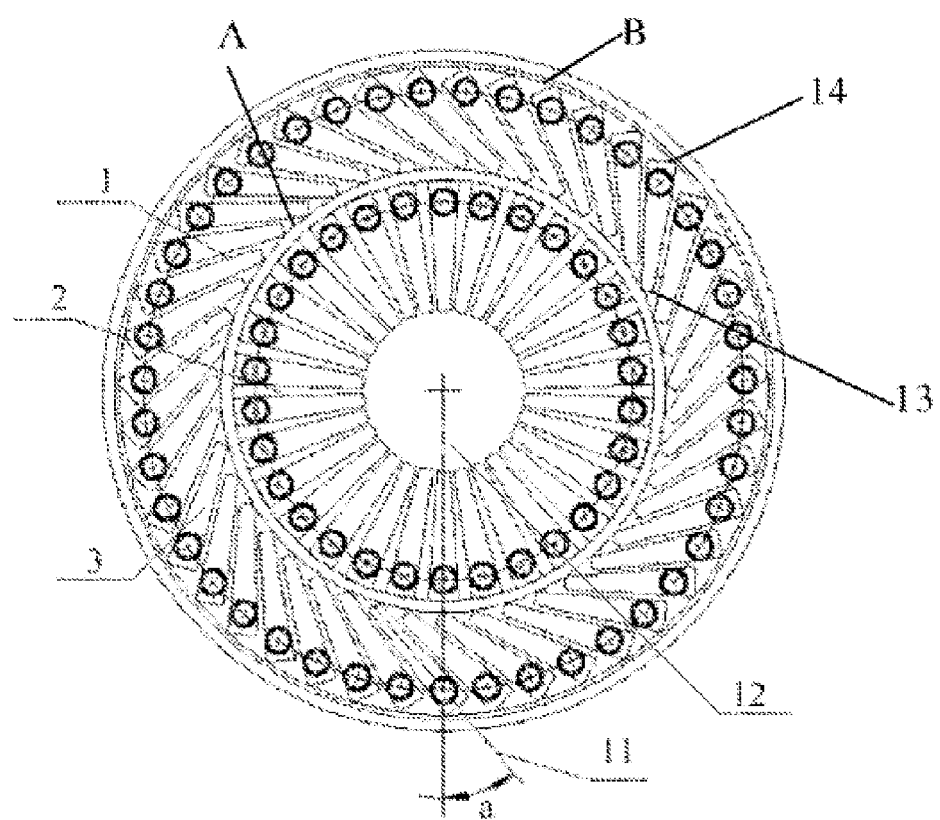
FIG. 2 is a top-down structure diagram for a reagent wheel in an embodiment of this disclosure.

As shown in FIG. 2, it illustrates a reagent wheel of an automatic analyzer in an embodiment of this disclosure. The reagent wheel can include a ring of reagent bottle seats 1 located on an outer ring and a ring of reagent bottle seats 2 located on an inner ring. All the reagent bottle seats 1 and 2 may have a circumferential distribution while taking a circle center of the reagent wheel as a center. The reagent wheel can rotate about its axle center, where the circle center of the reagent wheel may be set as the axle center. The reagent bottle seats 1 and 2 can be used for positioning and accommodating a reagent container 3. Symmetrical centerlines 11 of the reagent bottle seats 1 and 2 can completely or substantially overlap with that of the reagent container 3 placed on the reagent bottle seat. The reagent container 3 may be symmetrical with respect to its own symmetrical centerline 11, where the symmetrical centerline 11 may be orthogonal to an axis of the reagent container.

The respective reagent container 3 may be located by an included angle with respect to a radius of the reagent wheel. For such reagent container 3, its proximal end face 13 proximate to the circle center of the reagent wheel can be located on a circumference A, while its distal end face 14 away from the circle center of the reagent wheel may be located on another circumference B. That is, the reagent container 3 can be located between the two circumferences described above. The symmetrical centerline 11 of the reagent container 3 may be equivalent to a distance line of the reagent container, where the distance line may be a line segment representing a vertical distance between the proximal end face 13 and the distal end face 14.

The circle center, the center and the symmetrical centerline described above can be a corresponding projection of a line or a surface onto a surface that is perpendicular to the axis of the reagent wheel.

For the respective reagent container placed on the outer ring of reagent bottle seats 1, an included angle a ranging from about 0 degree to about 180 degree may be formed between the symmetrical centerline 11 of the reagent container and the radius 12 of the reagent wheel. In this embodiment, the respective reagent container placed on each reagent bottle seat 1 on the outer ring may have the same included angle between its symmetrical centerline 11 and the radius of the reagent wheel. In this way, when using the reagent container with the same shape, the reagent container 3 and the reagent bottle seat 1 may occupy reduced space along the radius of the reagent wheel, such that the reagent wheel can be reduced in its diametric size. Meanwhile, since the reagent bottle seat 1 is obliquely arranged on the outer ring, fewer reagent bottle seat can be placed on the outer ring, and thus reduced quantity variance can be achieved between the reagent bottle seat on the inner and the outer rings.

As an example, the included angle α shown in FIG. 2 can be about 40 degree, and there may be approximately 43 reagent bottle seats 1 on the outer ring correspondingly, which is comparable to the approximately 57 reagent bottle seats 1 on the outer ring illustrated in FIG. 1. When the reagent wheel is arranged as shown in FIG. 2, the resulting diametric size of the reagent wheel can be smaller than that of the reagent wheel in FIG. 1. That is, in case that the reagent wheel remains the same except arranging the reagent bottle seat 1 on the outer ring as described in various embodiments of this disclosure, the reagent wheel will be provided with smaller size, and reduced quantity variance can be achieved between the reagent bottle seat on the inner and the outer rings so as to meet the application requirement of the analyzer.

For the reagent container placed on the reagent bottle seat 2 on the inner ring, the symmetrical centerline of the reagent container can overlap with the radius of the reagent wheel, or an included angle may also be formed between the symmetrical centerline of the reagent container and the radius of the reagent wheel. The reagent container on the inner ring can be the same as each other; i.e., they can have the same size and volume. Alternatively, the reagent container on the inner ring can also have varied size and/or volume.

In order to solve the following problems: the capacity and the diametric size (i.e., operability) of the reagent wheel are not compatible with each other when two reagent wheels equipped with both an inner and an outer ring of reagent seats are placed one behind the other, the reagent bottle seats can be differently arranged on the inner ring and the outer ring, where the symmetrical centerline of the reagent container placed on the reagent bottle seat on the inner ring may overlap with the radius of the reagent wheel, and the included angle ranging from about 0 degree to about 180 degree may be formed between the symmetrical centerline of the reagent container placed on the reagent bottle seat on the outer ring and the radius of the reagent wheel. In this case, when the inner ring of the reagent wheel remains the same size, both the capacity and the diametric size of the outer ring of the reagent wheel can be slightly reduced.

In case that the reagent wheel with double rings is applied within the automatic analyzer equipped with two sets of test systems, it may be required that not only the total capacity on the double rings of the reagent wheel should be high, but also the differences should be as small as possible between the capacities of the inner and the outer rings. The capacity of the inner ring may limit the total capacity of the reagent wheel, while the diametric size of the outer ring of the reagent wheel may directly affect a whole diametric size of the reagent wheel (i.e., the limit of the operability for picking up and/or placing down the reagent). Since the outer ring may have had larger capacity than the inner ring, there may be no need to achieve more reagent capacity on the outer ring of the reagent wheel. Instead, when the capacity on the outer ring of the reagent wheel is reduced properly, smaller capacity differences between the inner and the outer rings can be obtained and the diametric size of the outer ring of the reagent wheel can also be reduced. When adopting the above-described arrangement for the reagent wheel, various embodiments of this disclosure can combine the diametric size of the reagent wheel (i.e., the operability), the capacity variance between the inner and the outer rings, and the total capacity of the reagent wheel.

The reagent wheel in various embodiments can be applied onto automatic analyzers. In a situation, two of such reagent wheels can be placed one behind the other, where each reagent wheel that may rotate independently can include an inner ring and an outer ring, and reagent bottle seats on the inner and the outer rings may correspond to two sets of test systems within the analyzer. In any other alternative situation, such reagent wheel(s) can be applied within the analyzer(s) with various arrangement designs for the reagent wheel; for example, there can be a single ring, a double ring or a multiple ring of reagent bottle seats on the reagent wheel; there can be one, two or more reagent wheels equipped therein; two or more reagent wheels can be freely placed on a table; and/or the multiple rings of reagent bottle seats can rotate jointly or independently. No matter how the reagent wheel is arranged, it can be ensured that the size of a certain ring on the reagent wheel can be as small as possible while acceptably reducing the capacity of this ring on the reagent wheel through setting the symmetrical centerline of the reagent container placed on the reagent bottle seat to have an included angle with respect to the radius of the reagent wheel as describe in this disclosure. In case that the reagent container has the constant size and shape, the capacity and the size of the reagent wheel can be more compatible with each other. Besides, in an alternative situation, such reagent wheel can be applied in a following arrangement where the reagent wheel and a sample wheel can be arranged coaxially.

The inner ring and the outer ring of the reagent wheel can also be called an inner supporting rail and an outer supporting rail, the reagent bottle seat can also be called a reagent seat, and the reagent container can be called a reagent bottle as well.

The invention claimed is:

1. A reagent wheel assembly of an automatic analyzer, comprising a reagent wheel and a reagent container arranged on the reagent wheel; the reagent wheel comprises an inner ring and an outer ring of reagent bottle seats, wherein the inner ring is connectable to a first set of test system and the outer ring is connectable to a second set of test system; each reagent bottle seat is distributed on the reagent wheel along a circumferential direction, and the reagent container is capable of being placed on each reagent bottle seat;

wherein the reagent container placed on each reagent bottle seat has a distal end face away from a circle center of the reagent wheel and a proximal end face proximate to the circle center of the reagent wheel; a line segment representing a vertical distance between the distal end face and the proximal end face is defined as a distance line;

wherein the distance line of the reagent container placed on the outer ring of reagent bottle seat is arranged obliquely towards one side of a radius of the circle where the reagent wheel is located, and an included angle that is larger than 0 degree and smaller than 180 degree is formed between the distance line of the reagent container placed on the outer ring of reagent bottle seat and the radius of the circle where the reagent wheel is located; wherein the distance line of the reagent container placed on the inner ring of reagent bottle seat overlaps with the radius of the circle where the reagent wheel is located;

wherein the distance line of each reagent container placed on the outer ring of reagent bottle seats is arranged obliquely towards a same side of the radius of the circle where the reagent wheel is located to form a clockwise or a counterclockwise oblique arrangement.

2. The reagent wheel assembly of an automatic analyzer of claim 1, wherein equal included angles are formed between the distance line of each reagent container placed on the outer ring of reagent bottle seats and the radius of the circle where the reagent wheel is located.

3. The reagent wheel assembly of an automatic analyzer of claim 1, wherein the reagent container is bilaterally symmetrical with respect to a symmetrical centerline; the distance line is equivalent to the symmetrical centerline.

4. The reagent wheel assembly of an automatic analyzer of claim 1, wherein the distal end face of the reagent container is located on a circumference and the proximal end face of the reagent container is located on another circumference.

5. The reagent wheel assembly of an automatic analyzer of claim 1, wherein each reagent bottle seat on the inner ring and the outer ring has a same shape, and the reagent container placed on each reagent bottle seat has a same shape and a same volume.

* * * * *